US012753387B2

(12) United States Patent
Valenzuela et al.

(10) Patent No.: US 12,753,387 B2
(45) Date of Patent: Oct. 6, 2026

(54) METHODS FOR MANUFACTURE OF NEURONAL PRECURSORS

(71) Applicant: SKIN2NEURON PTY LTD, Sydney (AU)

(72) Inventors: Michael Valenzuela, Sydney (AU); Adam Johnson, Sydney (AU)

(73) Assignee: SKIN2NEURON PTY LTD, Sydney (AU)

( * ) Notice: Subject to any disclaimer, the term of this patent is extended or adjusted under 35 U.S.C. 154(b) by 427 days.

(21) Appl. No.: 18/273,655

(22) PCT Filed: Jan. 21, 2022

(86) PCT No.: PCT/AU2022/050027
§ 371 (c)(1),
(2) Date: Jul. 21, 2023

(87) PCT Pub. No.: WO2022/155708
PCT Pub. Date: Jul. 28, 2022

(65) Prior Publication Data

US 2024/0076614 A1 Mar. 7, 2024

(30) Foreign Application Priority Data

Jan. 22, 2021 (AU) ................................ 2021900142

(51) Int. Cl.
*C12N 5/0797* (2010.01)
*C12Q 1/54* (2006.01)

(52) U.S. Cl.
CPC ............. *C12N 5/0623* (2013.01); *C12Q 1/54* (2013.01); *C12N 2506/092* (2013.01)

(58) Field of Classification Search
CPC ............ C12N 5/0623; C12N 2506/092; C12N 2500/34; C12N 5/0628; C12N 2506/1376; C12N 2513/00; C12N 5/0666; C12Q 1/54; G01N 33/5073; G01N 33/5082; G01N 33/5088; C12M 3/00
See application file for complete search history.

(56) References Cited

U.S. PATENT DOCUMENTS

| | | | |
|---|---|---|---|
| 2008/0286243 A1 | 11/2008 | Kang et al. | |
| 2010/0159589 A1 | 6/2010 | Li et al. | |

FOREIGN PATENT DOCUMENTS

| | | | | |
|---|---|---|---|---|
| JP | 02242669 A | 9/1990 | | |
| JP | 2005502377 A | 1/2005 | | |
| JP | 2012529901 A | 11/2012 | | |
| WO | 2003024406 A2 | 3/2003 | | |
| WO | 2010149597 A2 | 12/2010 | | |
| WO | 2011050476 A1 | 5/2011 | | |
| WO | 2011144901 A1 | 11/2011 | | |
| WO | 2014120013 A1 | 8/2014 | | |
| WO | 2019092667 A1 | 5/2019 | | |
| WO | 2019241846 A1 | 12/2019 | | |
| WO | WO-2020165615 A1 * | 8/2020 | .......... | C12Q 1/6883 |
| WO | 2005071063 A1 | 8/2025 | | |

OTHER PUBLICATIONS

HiMedia Laboratories Pvt. Ltd. "William's Medium E—with L-Glutamine without Sodium bicarbonate", Product Information: Product Code:AT1125, Jan. 2011, 2 pages. (Year: 2011).*

Peng Wei et al., The force is strong with this one: Metabolism (over)powers stem cell fate, Howard Hughes Medical Institute, Published as: Trends Cell Biol., Jul. 2018, vol. 28, No. 7, pp. 551-559, Salt Lake City, Utah, USA (14 pages).

Athanasia D. Panopoulos et al., The metabolome of induced pluripotent stem cells reveals metabolic changes occurring in somatic cell reprogramming, Cell Research (2012), vol. 22, pp. 168-177 (10 pages).

Rebecca Williams et al., Metabolism of Freshly Isolated Human Hair Follicles Capable of Hair Elongation: A Glutaminolytic, Aerobic Glycolytic Tissue, Journal of Investigative Dermatology (1993), vol. 100, No. 7, pp. 834-840 (7 pages).

Alonso L. et al., "The hair cycle." J Cell Sci. Feb. 1, 2006;119(Pt 3):391-3.

Belicchi M. et al., "Human skin-derived stem cells migrate throughout forebrain and differentiate into astrocytes after injection into adult mouse brain." J Neurosci Res. Aug. 15, 2004;77(4):475-86.

Biernaskie J. et al., "Isolation of skin-derived precursors (SKPs) and differentiation and enrichment of their Schwann cell progeny." Nat Protoc. 2006;1(6):2803-12.

Botchkarev V. et al, "Noggin is required for induction of the hair follicle growth phase in postnatal skin." FASEB J. Oct. 2001;15(12):2205-14.

Campos L.S. "Neurospheres: insights into neural stem cell biology." J Neurosci Res. Dec. 15, 2004;78(6):761-9.

Clewes O. et al., "Human epidermal neural crest stem cells (hEPI-NCSC)—characterization and directed differentiation into osteocytes and melanocytes." Stem Cell Rev Rep. Nov. 2011;7(4):799-814.

Couillard-Despres S. et al., "Human in vitro reporter model of neuronal development and early differentiation processes." BMC Neurosci. Feb. 29, 2008;9:31.

Dietrich J. et al., "Clinical patterns and biological correlates of cognitive dysfunction associated with cancer therapy." Oncologist. Dec. 2008;13(12):1285-95.

Duncant T. et al., "Replicable Expansion and Differentiation of Neural Precursors from Adult Canine Skin." Stem Cell Reports. Aug. 8, 2017;9(2):557-570.

Foitzik K. et al., "The TGF-beta2 isoform is both a required and sufficient inducer of murine hair follicle morphogenesis." Dev Biol. Aug. 15, 1999;212(2):278-89.

Fuchs E. "Skin Stem Cells in Silence, Action, and Cancer." Stem Cell Reports. May 8, 2018;10(5):1432-1438.

Ge Y. et al., "Stem Cell Lineage Infidelity Drives Wound Repair and Cancer." Cell. May 4, 2017;169(4):636-650.e14.

Gho C. et al., "Isolation, expansion and neural differentiation of stem cells from human plucked hair: a further step towards autologous nerve recovery." Cytotechnology. Oct. 2016;68(5):1849-58.

(Continued)

*Primary Examiner* — Aaron J Kosar
(74) *Attorney, Agent, or Firm* — Morgan, Lewis & Bockius LLP

(57) ABSTRACT

The present invention is directed to methods for determining the likelihood that source tissue will be suitable for the generation of viable precursor cells.

18 Claims, 4 Drawing Sheets

(56) References Cited

OTHER PUBLICATIONS

Hsu Y.C. et al., "Emerging interactions between skin stem cells and their niches." Nat Med. Aug. 2014;20(8):847-56.
Hwang I. et al., "Neural Stem Cells Restore Hair Growth Through Activation of the Hair Follicle Niche." Cell Transplant. 2016;25(8):1439-51.
Joannides A., et al., "Efficient generation of neural precursors from adult human skin: astrocytes promote neurogenesis from skin-derived stem cells." Lancet. Jul. 10-16, 2004;364(9429):172-8.
Kandyba E., et al., "Competitive balance of intrabulge BMP/Wnt signaling reveals a robust gene network ruling stem cell homeostasis and cyclic activation." Proc Natl Acad Sci U S A. Jan. 22, 2013;110(4):1351-6.
Lin H.Y. et al., "Differential response of epithelial stem cell populations in hair follicles to TGF-β signaling." Dev Biol. Jan. 15, 2013;373(2):394-406.
Najafzadeh N. et al., "In vitro neural differentiation of CD34 (+) stem cell populations in hair follicles by three different neural induction protocols." In Vitro Cell Dev Biol Anim. Feb. 2015;51(2):192-203.
Oshimori N. et al., "Paracrine TGF-β signaling counterbalances BMP-mediated repression in hair follicle stem cell activation." Cell Stem Cell. Jan. 6, 2012;10(1):63-75.
Pang Z.P. et al., "Induction of human neuronal cells by defined transcription factors." Nature. May 26, 2011;476(7359):220-3.
Plikus M.V. "New activators and inhibitors in the hair cycle clock: targeting stem cells' state of competence." J Invest Dermatol. May 2012;132(5):1321-4.
Sakaue M. et al., "Human epidermal neural crest stem cells as a source of Schwann cells." Development. Sep. 15, 2015;142(18):3188-97.
Sieber-Blum M. et al., "Pluripotent neural crest stem cells in the adult hair follicle." Dev Dyn. Oct. 2004;231(2):258-69.
Son E.Y. et al., "Conversion of mouse and human fibroblasts into functional spinal motor neurons." Cell Stem Cell. Sep. 2, 2011;9(3):205-18.
Stenn K.S. et al., "Controls of hair follicle cycling." Physiol Rev. Jan. 2001;81(1):449-494.
Toma J.G. et al., "Isolation of multipotent adult stem cells from the dermis of mammalian skin." Nat Cell Biol. Sep. 2001;3(9):778-84.
Toma J.G. et al., "Isolation and characterization of multipotent skin-derived precursors from human skin." Stem Cells. Jun.-Jul. 2005;23(6):727-37.
Truong A. et al., "Modeling neurodegenerative disorders in adult somatic cells: A critical review." Front. Biol. 11, 232-245 (2016).
Tsunemoto R et al., "Diverse reprogramming codes for neuronal identity." Nature. May 2018;557(7705):375-380.
Valenzuela M.J. et al. "Neural precursors from canine skin: a new direction for testing autologous cell replacement in the brain." Stem Cells Dev. Dec. 2008;17(6):1087-94.
Vasyliev R.G. et al., "Large-scale expansion and characterization of human adult neural crest-derived multipotent stem cells from hair follicle for regenerative medicine applications." Exp Oncol. Sep. 2017;39(3):171-180.
Vierbuchen T. et al., "Direct conversion of fibroblasts to functional neurons by defined factors." Nature. Feb. 25, 2010;463(7284):1035-41.
Yang H. et al., "Epithelial-Mesenchymal Micro-niches Govern Stem Cell Lineage Choices." Cell. Apr. 20, 2017;169(3):483-496. e13.
Yu H. et al., "Isolation of a novel population of multipotent adult stem cells from human hair follicles." Am J Pathol. Jun. 2006;168(6):1879-88.
Yu H. et al., "Stem cells with neural crest characteristics derived from the bulge region of cultured human hair follicles." J Invest Dermatol. May 2010;130(5):1227-36.
Zhou D. et al., "Conversion of fibroblasts to neural cells by p53 depletion." Cell Rep. Dec. 24, 2014;9(6):2034-42.
International Search Report dated Aug. 23, 2019, issued for International Application No. PCT/AU2019/050637.
Kealey T. et al., "The human hair follicle engages in glutaminolysis and aerobic glycolysis: implications for skin, splanchnic and neoplastic metabolism." Skin Pharmacol. 1994;7(1-2):41-6.
Lobo M. et al., "Nestin, a neuroectodermal stem cell marker molecule, is expressed in Leydig cells of the human testis and in some specific cell types from human testicular tumours." Cell Tissue Res. May 2004;316(3):369-376.
"Adherent Cell Culture vs. Suspension Cell Culture." ThermoFisher Scientific (2020), 3 pages.
Wu J. et al., "Enzyme digestion to isolate and culture human scalp dermal papilla cells: a more efficient method." Arch Dermatol Res. Jun. 2005;297(2):60-67.
Extended European Search Report dated Dec. 6, 2024, issued for the counterpart application No. EP 22741959.5.
Michael P. Philpott et al., Metabolic Studies on Isolated Hair Follicles: Hair Follicles Engage in Aerobic Glycolysis and Do Not Demonstrate the Glucose Fatty Acid Cycle, J Invest Dermatol. Jun. 1991, vol. 96, No. 6, pp. 875-879. doi: 10.1111/1523-1747. ep12475232.
Office Action dated May 14, 2026, issued in counterpart Japanese Patent Application No. 2023-544342 (6 pages).

* cited by examiner

METHODS FOR MANUFACTURE OF NEURONAL PRECURSORS

FIELD OF THE INVENTION

The present invention is directed to methods for determining the likelihood that source tissue will be suitable for the generation of viable precursor cells.

RELATED APPLICATION

This application claims priority from Australian provisional application AU 2021900142, the entire contents of which are hereby incorporated by reference.

BACKGROUND OF THE INVENTION

A major challenge in the practical development of cell-based therapies is cellular variability. Such variability can arise at multiple levels and from multiple sources: biological variability within and between source donor tissue, variability in transfection methods or even basic reagents, batch-to-batch variability (from the same cellular motherstock), line-to-line variability (between donors), clone-to-clone variability (within a line from the same donor), and of course even cell-to-cell variability within a cell population or within the same cell over time.

Theoretically, all such observed variance can be deconstructed into biological variability (which is intrinsic and hence cannot be eliminated), manufacture variability (which is by design and can be controlled and optimised) and technical error (which is also unavoidable but can be minimized).

Regardless of the cell type or manufacture process, source- or donor start-tissue variability is a major and unaddressed challenge. This, in effect, introduces a systematic component of variation into the manufacturing process at the outset and contributes to variance in the final cellular product. Moreover, current cell manufacture methods do not sufficiently understand this form of variance in order to introduce quality controls over it. In other words, current technology does not understand what biological feature to measure in the source tissue, in order to quantify how different is this donor tissue to the usual or ideal, nor govern the process with a control procedure over the final product ("does this donor source tissue meet the relevant criteria?").

There is a need for the identification of biomarkers which are predictive of the suitability of source tissue for use in the generation of viable precursor cells.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention is based on the discovery by the inventors of a predictive biomarker for the manufacture of human hair-follicle derived neuronal precursors based on source tissue.

Accordingly, in a first aspect, the present invention provides a method for determining whether source tissue is suitable for providing hair-follicle derived neural precursors (HFNs), the method comprising:

providing a reference glucose consumption profile from intact human hair follicles that have been demonstrated to generate a viable HFN cell line;

providing source tissue in the form of a sample of hair follicle cells;

determining the glucose consumption of the follicles in the sample;

comparing the glucose consumption of the follicles in the sample to the reference glucose consumption profile;

determining that the source tissue is suitable for providing hair-follicle derived neural precursors (HFNs) if the glucose consumption of the follicles is the same or higher than that of the reference glucose consumption profile.

Further, the present invention provides a method for determining whether source tissue is suitable for providing hair-follicle derived neural precursors (HFNs), the method comprising:

providing a reference glucose consumption profile from intact human hair follicles that have been demonstrated to generate a viable HFN cell line;

providing source tissue in the form of a sample of hair follicle cells;

determining the glucose consumption of the follicles in the sample;

comparing the glucose consumption of the follicles in the sample to the reference glucose consumption profile;

determining that the source tissue is likely not suitable for providing hair-follicle derived neural precursors (HFNs) if the glucose consumption of the follicles is lower than that of the reference glucose consumption profile.

It will also be appreciated that the reference glucose consumption profile used may be from one or more samples of intact hair follicles which were shown to not be suitable for the generation of viable HFNs. Accordingly, in a further aspect, the invention provides a method for determining whether source tissue is suitable for providing hair-follicle derived neural precursors (HFNs), the method comprising:

providing a reference glucose consumption profile from intact human hair follicles that did not generate a viable HFN cell line;

providing source tissue in the form of a sample of hair follicle cells;

determining the glucose consumption of the follicles in the sample;

comparing the glucose consumption of the follicles in the sample to the reference glucose consumption profile;

determining that the source tissue is suitable for providing hair-follicle derived neural precursors (HFNs) if the glucose consumption of the follicles is higher than that of the reference glucose consumption profile.

Further, there is provided a method for determining whether source tissue is suitable for providing a hair-follicle derived neural precursor (HFN) cell line, the method comprising:

providing a reference glucose consumption profile from intact human hair follicles that did not generate a viable HFN cell line;

providing source tissue in the form of a sample of hair follicle cells;

determining the glucose consumption of the follicles in the sample;

comparing the glucose consumption of the follicles in the sample to the reference glucose consumption profile;

determining that the source tissue is not suitable for providing hair-follicle derived neural precursors (HFNs) if the glucose consumption of the follicles is the same or lower than that of the reference glucose consumption profile.

The present methods therefore provide an improved method for the generation of neuronal precursor cells from a sample of hair follicles, the method comprising:

- treating a sample of hair follicles in conditions enabling the transition of hair follicle cells to a growth phase, thereby forming a sample of conditioned cells;
- determining the glucose consumption of the conditioned follicles;
- comparing the glucose consumption of the conditioned follicles to a reference glucose consumption profile representative of hair follicles that generated a viable HFN cell line;
- proceeding to treat the conditioned follicles in conditions enabling enrichment of the number of cells containing neuronal lineage biomarkers, if the glucose consumption of the conditioned follicles is the same or higher than that of the reference glucose consumption profile.

thereby generating a composition of neuronal precursor cells from a sample of hair follicles.

The present methods also provide an improved method for the generation of neuronal precursor cells from a sample of hair follicles, the method comprising:

- treating a sample of hair follicles in conditions enabling the transition of hair follicles to a growth phase, thereby forming a sample of conditioned cells;
- determining the glucose consumption of the conditioned follicles;
- comparing the glucose consumption of the conditioned follicles to a reference glucose consumption profile representative of hair follicles that did not generate a viable HFN cell line;
- proceeding to treat the conditioned follicles in conditions enabling enrichment of the number of cells containing neuronal lineage biomarkers, if the glucose consumption of the conditioned follicles is higher than that of the reference glucose consumption profile.

thereby generating a composition of neuronal precursor cells from a sample of hair follicles.

In any aspect, the glucose consumption of the hair follicles is preferably determined within about 1 to 72 hours, preferably within about 12 to 24 hours of collection of isolation or harvesting of the source tissue from the tissue donor.

In any aspect, the glucose consumption of the sample is preferably determined from intact (whole) hair follicles.

As such the glucose consumption of the follicles is preferably determined prior to a step of dissociation of the hair follicles from connective tissue, extracellular matrix and optionally terminally differentiated cells.

In any embodiment, the conditions for treating the sample of hair follicle cells enables transition of the hair follicle precursor cells in the sample to transition from telogen to anagen phase. Preferably, such conditions comprise treating the hair follicle sample with an anti-refractory hair follicle factor and/or pro-growth factor, as further described herein.

The conditions enabling enrichment of the number of cells containing neuronal lineage biomarkers preferably comprise culturing the conditioned cells in culture medium and conditions for promoting the formation and expansion of neurospheres. Methods for neurosphere formation are generally well known in the art and exemplified further herein. In particularly preferred embodiments the conditions for promoting formation and expansion of neurospheres comprises culturing the cells in medium that comprises epidermal growth factor (EGF), fibroblast growth factor (FGF) especially basic FGF being FGF2 and optionally a neuronal cell culture supplement such as B2® supplement.

The reference glucose consumption profile may be derived from one or more samples of intact hair follicles that had previously been determined to provide for viable HFNs following downstream processing. Accordingly, the reference glucose consumption profile serves as a reference data set of glucose consumption profiles for intact hair follicles and that is indicative of a desirable balance between presence of precursor cells and the growth phase of the hair follicle, which in turn increases the likelihood that the hair follicle can be used to generate viable HFNs.

In any aspect, the method may comprise comparing the glucose consumption of hair follicles in a test sample to one or more glucose consumption profiles.

In any aspect, the sample of skin comprising hair follicle cells, or the sample of hair follicle cells is provided in cell culture medium suitable for supporting hair follicle cells. Preferably, the cell culture medium promotes transition of hair follicle precursor cells to a growth phase and is herein also referred to as "conditioning medium". Similarly, the conditions enabling the transition of hair follicle precursor cells to a growth phase will typically comprise culturing the hair follicles in cell culture medium suitable for supporting hair follicle cells. Williams medium E is one example of suitable medium for use for this purpose. Other examples include Dulbecco's modified eagle medium (DMEM) plus F-12 in different combinations, F12 plus mammalian serum in different combinations and different supplemented phosphate buffered saline combinations.

In one embodiment, the conditioning medium comprises Williams' E medium. Preferably, the Williams' E medium is supplemented with one or more anti-refractory factors and/or one or more pro-growth factors. In certain embodiments, the Williams' E medium is supplemented with one or more of insulin, sonic hedgehog, noggin and TGF-β. In particularly preferred embodiments, the culture medium comprises Williams' E medium supplemented with at least insulin and sonic hedgehog.

In any aspect, the conditions enabling the transition of hair follicles to a growth phase comprises culturing the follicles in cell culture medium suitable for supporting hair follicles. In one embodiment, the medium comprises Williams E medium. Preferably, the Williams' E medium is supplemented with one or more anti-refractory factors and/or one or more pro-growth factors. In certain embodiments, the Williams' E medium is supplemented with one or more of insulin, sonic hedgehog, noggin, and TGF-β. In particularly preferred embodiments, the culture medium comprises Williams' E medium supplemented with at least insulin, and sonic hedgehog.

In any aspect of the invention, the glucose consumption profile of the sample (or of the reference profile) is determined by directly measuring the rate of glycolysis of the follicles. Alternatively, glucose consumption may be determined indirectly, and derived following the measurement of the change in an alternative biomarker, which is indicative of the rate of glucose consumption (glycolysis). Such alternative measures of glucose consumption are further described herein and are known to the skilled person.

In preferred embodiments, the reference glucose consumption profile comprises data on the number of target cells normalised to the number of live cells at HF dissociation, and relative glucose consumption.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
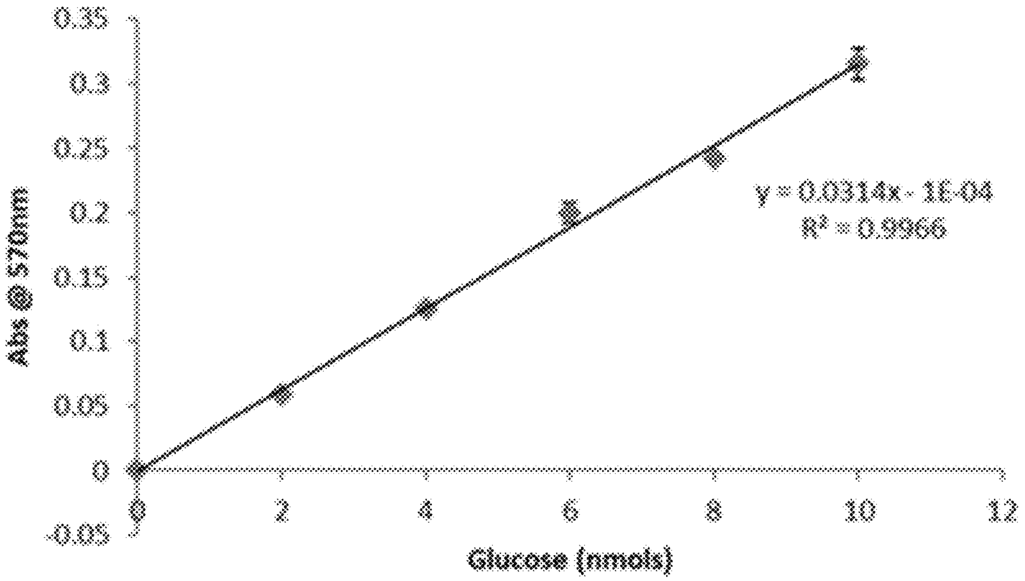
FIG. 1: The output of the glucose optical assay is highly correlated with actual glucose concentration. Standards were prepared in duplicate as per manufacturer's instructions. The values were averaged and zeroed and plotted in Excel. Linear regression produced a correlation coefficient of 0.9966

The present invention builds on earlier work by the inventors, directed to methods for the production of neuronal precursor cells from human skin samples derived from the scalp. The present invention provides a means for assessing, within only a short period following harvesting of donor tissue, whether the tissue will provide a suitable source of neuronal precursor cells.

Advantageously, the present invention enables the researcher or clinician preparing neuronal precursor cells, to determine whether the source tissue provides a source of viable precursor cells, prior to dissociation of the hair follicles from extracellular matrix, connective tissue and depletion of terminally differentiated cells. In other words, glucose consumption can be determined from intact hair follicles. Thus, the methods enable an assessment of the quality of the source tissue in as little as 12-24 hours post-harvest.

Methods for the isolation of neuronal progenitor cells derived from hair follicles are generally described in WO 2019/241846, the entire contents of which are hereby incorporated by reference.

As used herein, the terms hair follicle neuroprecursor (HFN), hair follicle neuronal precursor and hair follicle neuronal progenitor cells will be understood to be used interchangeably.

Thus, the present invention provides for methods for quality control during the process of preparation of HFNs, comprising a step of assessing glucose consumption by hair follicle cells shortly after isolation of the donor tissue and prior to further tissue processing.

Moreover, the present invention also improved methods for the generation of HFNs, by the inclusion of a step of determining glucose utilisation, thereby enabling a more efficient approach for the manufacture of HFNs.

Isolation of Intact Hair Follicles

Hair follicles may be obtained from a sample of skin comprising hair follicles. Typically, hair follicles are obtained by harvesting of a skin sample that contains hair follicle units. It is preferred that the sample is obtained from human scalp skin that contains the highest and most uniform hair follicle density, preferably midline occipital scalp skin. This skin generally contains a higher density of active hair follicles from individual to individual.

The cells of the hair follicles generally include precursor and stem cells from different niches, including the bulge area, the germ zone and the dermal papillae, collectively referred to as hair follicular precursors. Hair follicular precursors can express neuro-ectodermal biomarkers.

The harvested hair follicles are then treated in conditions promoting transition to a growth phase. The step is important because it contributes to increased yield of neural precursor cells. Preferably, the skin sample is transitioned into these conditions as soon as possible following harvest, preferably within about 1 to 24 hours following harvest, more preferably within about 2 to 12, most preferably within about 2 to 6 hours.

Culture Medium

In preferred embodiments, the intact hair follicle, or sample of skin comprising hair follicles is treated in conditioning medium prior to determining the glucose consumption of the cells therein.

The conditioning medium is typically any cell culture medium that supports cell survival of cells of the skin sample and enables the transition of cells to an anagen phase (or active growth phase of the follicle cell cycle). The conditioning medium also is one that supports the in vitro viability of epithelial cells and hair follicular organogenesis. Williams' Medium E is one example of suitable medium. Other examples include Dulbecco's modified eagle medium (DMEM) plus F-12 in different combinations, F12 plus mammalian serum in different combinations and different supplemented phosphate buffered saline combinations As used herein, Williams' E Medium (also referred to as Williams Medium E) is described in Williams, G. M., Weisburger, E. K. and Weisburger, J. H. 1971. Exptl. Cell Res. 69, 106. William's Medium E was developed in 1971 to be used as a reduced serum-supplemented medium with enriched amino acids and double the glucose for long-term cell cultures of adult rat liver epithelial cells. William's Medium E unique components include zinc, iron, manganese, non-essential amino acids, the reducing agent glutathione and the lipid methyl linoleate. Williams' E Medium may also comprise glucose (up to 2 mM) and L-glutamine.

Williams' E Medium can be obtained from various commercial suppliers including Sigma-Aldrich (W4128), Lonza (BE02-019F), Fisher Scientific (10137414).

Anti-refractory hair follicle factors and/or pro-growth factors may be utilised for promoting transition of hair follicle precursor and stem cells to anagen phase, thereby enabling the transition of hair follicle cells in the skin to a growth phase. Examples of anti-refractory hair follicle factors include noggin or sonic hedgehog (SHH) or factors that activate that Wnt1 signalling pathway, or that inhibit the bone morphogenic protein (pro-refractory) stimulus. Other examples of anti-refractory factors include WNTs, as well as BMP antagonists such as Grem 1 and Bambi. TGF-β2 is a key pro-growth factor; other examples of pro-growth factors include FGF7, FGF10 and platelet-derived growth factor (PDGF).

Generally the intact hair follicle or sample of skin comprising the hair follicle will be treated in the conditioning medium for a period from about 12 to 100 hours, although in some circumstances, it may be possible to culture for a longer period of time. As further explained herein, the consumption of glucose by the cells in the conditioning medium is preferably determined between about 12 to 72 hours following exposure of the cells to the conditioning medium and the results thereof are useful for providing an indication of whether the hair follicle will be useful for generating viable HFNs.

Glucose Consumption Assays

It will be appreciated that any standard method for the determination of glucose consumption by cells can be utilised in accordance with the present invention. Typically, glucose consumption (glycolysis) by cells in culture can be determined by comparing the rate of glucose/glucose concentration present in the culture medium at different time points.

The skilled person will be familiar with various colorimetric, fluorometric, bioluminesent and radio-labelled methods for estimating glucose utilisation in vitro. Examples of such methods can be found in Yamamoto et al., (2015) Curr. Protoc. Pharmacol. 71: 12.14.1-22, Zou et al., (2005) J. Biochem. Biophys. Methods, 64: 207-215; Blake et al., (1989) Anal Biochem, 177: 156-60; Valley et al., (2016) Anal. Biochem. 505: 43-50; each incorporated herein by reference.

The skilled person will be familiar with various commercially available kits which are suitable for use in determination of glucose concentrations/differences in the amount of glucose in cell media at different time points, in order to make an assessment of the glycolytic capacity of the cells in culture.

Non-limiting examples of commercially available kits for determining glucose concentration in culture medium include: Abcam Glucose Assay Kit (ab65333), Cell Biolabs Glucose Assay Kit (STA-680), Sigma Aldrich Glucose Assay Kit (GAGO20, HAHK20, CBA086, MAK181), Merck Millipore Glucose Assay, BioAssay Systems EnxyGhrom Glucose Assay Kit (EBGL-100) and Glucose-Glo Assay (Promega, J6021 and J6022).

Moreover, it will be appreciated that in accordance with the methods of the present invention, glucose consumption of the hair follicles can be determined either directly or indirectly. For example, in certain embodiments, a glucose consumption profile can be determined for hair follicles by directly measuring consumption of glucose by the follicles using a glucose measurement assay as known to the skilled person or as described herein. In alternative embodiments, a "proxy" or "surrogate" marker of glucose consumption can be measured and can be used for inferring glucose consumption by the hair follicles. The skilled person will be familiar with various metabolites or associated biomarkers that can be correlated with glucose consumption and consequently, energy expenditure of the cells. Examples of such markers include: pyruvate, NADH, oxygen, lactate, ATP and other by-products of glucose metabolism. Accordingly, in certain embodiments of the invention, glucose consumption of hair follicles can be determined from the measurement of changes in the levels of one or more of: pyruvate, NADH, oxygen, lactate, ATP or of any other by-product of glucose metabolism.

Methods for measuring pyruvate, NADH, oxygen, lactate, ATP or of any other by-product of glucose metabolism are known in the art and can also be assessed using commercially available kits.

In particularly preferred embodiments of the invention, the glucose consumption profile (and the profile of the reference) is normalised to the number of cells in the hair follicle. This accounts for changes in glucose utilisation based on the size of the follicle and number of cells comprised therein.

Reference Glucose Consumption Profile

The present invention preferably includes a step of providing, obtaining or having been provided with a reference glucose consumption profile. It will be appreciated that the glucose consumption profile functions as a reference standard for the degree of glucose consumption that is indicative that hair follicles (or a skin sample comprising hair follicles) will give rise to viable HFNs, or a sufficient number of viable HFNs, such that the HFNs can be used in downstream clinical or research applications.

Preferably the reference glucose consumption profile is obtained from intact hair follicles that were ultimately found to be useful for the generation of viable and HFNs suitable for use in downstream clinical and research applications. However, in certain circumstances, it may also be useful or appropriate to consider a reference glucose consumption profile from hair follicles which did not give rise to viable or clinically useful HFNs.

Such reference glucose consumption profiles will aid in setting a benchmark of glucose consumption by hair follicles that is indicative of whether the hair follicles comprise sufficient precursor cells and precursor cells at the correct stage of growth (e.g., anagen phase) to facilitate production of HFNs following downstream processing. As such, by comparing the glucose consumption of a hair follicle sample to a glucose consumption profile as described herein, the skilled person is provided with a means for assessing early-on in the production process, whether the hair follicles will give rise to viable HFNs.

The skilled person will appreciate that the glucose consumption profile obtained from hair follicles (for use in the comparative steps of the invention), is to be correlated with the characteristics of the HFNs derived from those hair follicles following subsequent processing. The characteristics of viable and useful HFNs are further described herein.

In any embodiment, the methods of the invention may include firstly obtaining a glucose consumption profile by deriving HFNs from a series of intact hair follicles in order to derive a reference data set, determining whether the HFNs obtained were viable/suitable/in sufficient number for downstream applications and then identifying a rate of glucose consumption for hair follicles that is indicative (or not) that viable HFNs could be obtained therefrom. Alternatively, the methods include reviewing/observing/reading one or more glucose consumption profiles that are stored on a database and correlated with successful HFN isolation.

The methods of the present invention preferably comprise comparing the glucose consumption of conditioned cells obtained from a sample of hair follicles, to a reference glucose consumption profile representative of hair follicles that generated viable HFNs. The comparison involves determining whether glucose consumption of the conditioned cells is higher, lower or the same as the glucose consumption profile (or reference standard).

In any embodiment, a "higher" rate of glucose consumption compared to the profile or reference standard, will be understood to include a rate that is at least about a 1.5-fold, 2-fold, 2.5-fold, 3-fold, 3.5-fold, 4-fold, 4.5-fold, or 5-fold or faster, compared to the profile or reference standard.

In any embodiment, a "lower" rate of glucose consumption compared to profile or reference standard will be understood to include a rate that is at least about a 1.5-fold, 2-fold, 2.5-fold, 3-fold, 3.5-fold, 4-fold, 4.5-fold, or 5-fold, or slower, compared to profile or reference standard.

In any embodiment, a "higher" rate of glucose consumption compared to the profile or reference standard, will be understood to include a degree of glucose consumption that is at least about 15%, 20%, 30%, 40%, 50%, 60%, 70%, 80%, 90%, 100% or faster than the rate of the glucose consumption profile or reference standard.

In any embodiment, a "lower" rate of glucose consumption compared to the profile or reference standard, will be understood to include a rate of glucose consumption that is at least about 15%, 20%, 30%, 40%, 50%, 60%, 70%, 80%, 90%, 100% or slower than the glucose consumption profile or reference standard.

In any embodiment, a rate of glucose consumption that is the "same as" the glucose consumption profile or reference standard, will be understood to include a rate of glucose consumption that is at least about 1%, 2%, 3%, 4%, 5% or 10% more or less than the glucose consumption profile or reference standard.

In particularly preferred embodiments, the glucose consumption profile is normalised to a glucose consumption range of between about 0.1 μmol/follicle/24 hours to about 0.9 μmol/follicle/24 hours. Typically, a desirable glucose consumption rate in hair follicles (i.e., being indicative that the hair follicles will give rise to viable HFNs of suitable number for downstream processing), corresponds to a glucose consumption of at least about 0.6 μmol/hair follicle/24 hours, preferably at least about 0.7 μmol/hair follicle/24 hours, or at least about 0.8 μmol/hair follicle/24 hours or more.

In a further aspect the present invention provides a method for identifying source tissue as suitable for providing hair-follicle derived neural precursors (HFNs), the method comprising:

- providing source tissue in the form of a sample of hair follicle cells;
- determining the glucose consumption of the cells in the sample;
- determining that the source tissue is suitable for providing hair-follicle derived neural precursors (HFNs) if the glucose consumption of the cells is at least about 0.6 μmol/hair follicle/24 hours, preferably at least about 0.7 μmol/hair follicle/24 hours, or at least about 0.8 μmol/hair follicle/24 hours or more.

In a further aspect the present invention provides a method for identifying source tissue as suitable for providing hair-follicle derived neural precursors (HFNs), the method comprising:

- providing source tissue in the form of a sample of skin comprising hair follicle cells;
- determining the glucose consumption of the cells in the sample;
- determining that the source tissue is suitable for providing hair-follicle derived neural precursors (HFNs) if the glucose consumption of the cells is at least about 0.6 μmol/hair follicle/24 hours, preferably at least about 0.7 μmol/hair follicle/24 hours, or at least about 0.8 μmol/hair follicle/24 hours or more.

Dissociation and Neurosphere Culture

Prior to generating neurospheres and HFNs from the intact hair follicle, it is generally desirable to remove the extracellular matrix and non-cellular components of the skin tissue, in which the progenitor cells are entrapped (in other words, to dissociate the progenitor cells present in the intact hair follicle from skin components). Optionally the dissociation step may also comprise a step of reducing or removing terminally differentiated cells, such as fibroblasts.

Standard methods known to the skilled person can be employed for the dissociation of hair follicles from skin tissue can be utilised. In certain examples, the methods comprise resuspending the intact hair follicles in a solution of enzymes. Generally, the enzymes may be one or more selected from the group consisting of trypsin, DNase, dispase, collagenase, and combinations of Accustase and TrypLE.

Depending on the nature of the conditioned skin, it may alternatively be possible to release cells from the conditioned skin by mechanical means that mince or separate tissue into smaller particles by disrupting the conditioned tissue.

In some embodiments, the cells are released from the conditioned skin by a combination of enzymatic and mechanical treatment (which may be gentle trituration). The enzymatic and mechanical treatment may occur at the same time, although generally the enzymatic treatment is initiated before the mechanical treatment is initiated.

Following enzymatic and/or mechanical treatment to dissociate hair follicles from tissue components, the solution may be filtered and/or centrifuged to further remove connective tissue and extracellular matrix from the cells.

The composition of cells obtained from the sample of skin/intact hair follicle is heterogeneous, and comprises neuronal precursor cells, other distinct multipotent cells, and terminally differentiated cells including fibroblasts, keratinocytes and other cells of the epidermal and dermal layers of skin tissue, depending on from where the tissue was harvested. Accordingly, in certain embodiments, the methods of the invention include a step of removal of cells that are non-neural precursor cells from the composition of cells released from the conditioned human skin. The cells to be removed are typically terminally differentiated cells (i.e. keratinocytes, fibroblasts, other dermal and epidermal cells and apoptotic cells.

In one embodiment, the terminally differentiated cells are depleted from the sample by contacting the sample with a reagent for selectively depleting terminally differentiated cells. Preferably the agent is an antibody that binds to terminally differentiated cells but not to non-terminally differentiated cells. Antibody treatments, preferably using a monoclonal antibody that does not bind to neural precursor cells, is effective for this step. Preferably the antibody binds to cells of the epidermis or dermis such as keratinocytes, or to fibroblasts. Examples of such antibodies may include those that selectively bind to fibroblast-specific antigen 1, or to CD45, these not being antigens found on the surface of neuronal precursor cells.

At the completion of the depletion step, the sample typically contains no more than about 5% by number of terminally differentiated cells, optionally no more than about 10%, no more than about 15%, no more than about 20% terminally differentiated cells.

Following dissociation or depletion steps as described above, the cells are typically transferred to growth medium for promoting the formation of neurospheres. In other words, the cells are cultured in conditions for promoting or increasing the number of cells comprising neuronal lineage biomarkers, and/or decreasing the proportion or number of cells that do not contain neuronal lineage biomarkers.

In a particularly preferred step, the cells are treated in conditions enabling the formation of neurospheres. Methods for neurosphere formation are generally well known in the art and exemplified further herein. In one embodiment, the cells are treated to enrich or otherwise to increase the number of cells containing neuronal lineage biomarkers, or to enable the formation of neurospheres by culturing the cells in a bioreactor. A bioreactor may be utilised to provide improved conditions for formation of neurospheres.

Growth medium for enabling the promotion of neurospheres is also generally well known in the art. In certain embodiments, the growth medium comprises DMEM/F12, EGF, bFGF and B27.

At the completion of the formation of neurospheres, it may be advantageous to increase the number of cells of the neurospheres that are neural precursor cells, or that express neural lineage biomarkers, by an expansion step. Methods for expanding neurospheres in culture are also known in the art.

The HFNs produced by the improved methods of the present invention are neuronal precursor cells or more generally proliferating cells that express neural lineage biomarkers. Neural lineage biomarkers cover a developmental spectrum that can include (most primitively) neural stem cell-like marker nestin, neuroblastic markers doublecortin (DCX) and NCAM and immature neuron marker betaIII-tubulin. More generic stem cell-like markers such as CD133 can also be expressed. Cells positive for these markers are enriched in neurospheres and that have potential to form terminally differentiated neurons. Generally, these cells have potency for the generation of terminally differentiated cells of the neural lineage, such as neurons and glia.

It will be appreciated that HFNs that are considered "viable" (and therefore which are used for the purposes of identifying an appropriate glucose consumption profile for use in accordance with the methods of the invention) will have certain preferred characteristics and more generally, are proliferating cells that express neural lineage biomarkers, as recited above.

Typically, a population of neuronal precursors (HFNs) produced by the improved methods of the invention (or which are considered viable and therefore useful for associating with hair follicles having a particular a glucose consumption profile), will comprise <5% of cells that express the markers adiponectin, oligodendrocyte 04, myofibroblast SMA and/or GFAP. The population of HFNs typically comprise >90% of cells that are positive for the markers nestin, CD133 (promonin-1), CD271 (P75NTR), neurofilament and/or βIII-tubulin.

In particularly preferred embodiments, viable HFNs, or HFNs that are particularly suitable for downstream clinical and research application, will be hair-follicle derived neuroprecursor cells that are positive for one or more, preferably at least two, at least three, at least 4 or all of the following protein markers: nestin, CD133 (promonin-1), CD271 (P75NTR), and βIII-tubulin or neurofilament. Further, viable HFNs, or HFNs that are particularly suitable for downstream clinical and research application, will be hair-follicle derived neuroprecursor cells that are also negative for one or more, preferably at least two, at least three, or all of the following protein markers: GFAP, K14/15, SOX2 and OCT3/4.

Viability of HFNs may also be determined using other known methods in the art, including functional properties such as chemotaxis towards neuronal growth factors, and electrophysiological activity after differentiation. Such functional characteristics are well known to the skilled person and described in the prior art.

EXAMPLES

Example 1: Materials and Methods

Biological Samples

Human skin samples were obtained with informed consent from patients undergoing hair transplant surgery. The tissues were collected under sterile conditions at the time of surgery. Generally, the donor's posterior scalp was shaved and a 1×3 cm sample was taken at full thickness down to the fatty layer using a dual-blade scalpel. For hair follicle extraction, the whole dermis tissue was rapidly and progressively cut down into individual follicles under direct microscopy to isolate approximately 100 hair follicles. The skin and follicle tissues were stored in holding media (William's E medium containing insulin and Antibiotic-Antimycotic) and transported on ice to the laboratory as quickly as possible for immediate processing.

The HFN cell lines used for experiments here were from 5 independent donors aged 32-57 years.

HFN Cell Manufacture Process

HFN manufacture was according to the process described in WO 2019/241846. Briefly, following tissue arrival at the lab, the follicles were centrifuged and washed.

Cells were transferred to conditioning media (as described herein) and a 1 mL sample of medium was taken and frozen to serve as 0 h control. The follicles were suspended in pre-warmed conditioning media and then incubated at 37° C./5% $CO_2$ for 24 hours. At 24 hours a 1 mL aliquot of media was taken from each sample and frozen, while the remaining media was discarded and replaced with pre-warmed freshly made conditioning media (of which another control sample was taken). After a further 24 hours another media sample was taken and the follicles were dissociated, purified and expanded.

Dissociation and Neurosphere Culture

Following enrichment, the follicles were centrifuged to remove conditioning medium and the follicles resuspended in a solution collagenase/dispase solution to release precursor cells from extracellular matrix and connective tissue. Cells were transferred to warm HFN growth media (as described herein). 10 μL aliquots of the cell suspension were used to perform cell number and viability count using Trypan blue. For HFN neurosphere culture, cells were seeded at $2\times10^5$ cells/mL in a total of 5 mL growth media into uncoated and untreated 6-well plates.

Suspension cultures were incubated at 37° C./5% $CO_2$ and monitored every 2-3 days for neurosphere formation. Once neurospheres reached 30-50 μm in diameter (usually by day 2 or 3 post-seeding), the sphere suspension was transferred to a bioreactor unit (ABLE Biott, ReproCell). The bioreactor wells were monitored daily for sphere growth. At around day 5 or 7, the sphere suspension was collected and centrifuged. An equal volume of pre-warmed HFN growth media was added to the cells and 10 μL aliquots were used to perform cell number and viability count of target cells using Trypan blue. For subsequent HFN adherent cultures, cells were seeded into biolaminin-coated 6-well plates. The next day, medium containing TryPLE Select was replaced with fresh HFN growth medium. Growth was monitored to confirm morphology of target cell type.

Example 2: Determination of Glucose Usage

Deproteinization of Samples

All samples were defrosted and transferred to Abcam 10 kD spin columns (ab93349) and centrifuged at 10,000×g for 10 minutes at 4° C. The filtrate was collected and used for glucose assay.

Glucose Assay

The glucose assays were performed using the Abcam Glucose Assay Kit (ab65333) according to manufacturer's instructions. Briefly, deproteinised control (0 h) and 24 h samples, along with background control samples were diluted 1 in 10, 1 in 100 and 1 in 1000 with assay buffer and added into individual wells of a 96 well plate. Glucose standards were prepared and run in the same plate. All samples and standards were run in duplicate. Final volume for all standards and sample dilutions was 50 μL. For each well, 50 μL reaction mixture or 50 μL Background reaction mixtures were prepared as follows:

| Component | Reaction mix μL | Background reaction mix μL |
|---|---|---|
| Glucose assay buffer | 46 | 48 |
| Glucose probe | 2 | 2 |
| Glucose enzyme mix | 2 | 0 |

50 μL of reaction mixture was added and mixed into each standard and sample and 50 μL Background reaction mixture was added and mixed into each background control sample. The plate was incubated for 30 minutes at 37° C. protected from light. The optical density at 570 nm of each well was then determined using a microplate reader. The sample readings were zeroed by subtracting the blank adjusted background reaction mixture OD from the sample reading. The blank standard was subtracted from the standards and a standard curve was constructed. The standard curve was rejected if the r2 for the line generated was less than 0.99. The sample dilution that fell on the standard curve was used. Glucose content of samples was calculated using the line formula generated by the standard curve and corrected by multiplying by the original dilution factor of the sample. Glucose consumption at 24 hours and 48 hours was calculated by subtracting the glucose present in the 24 h or 48 h samples from the 0 h control samples. 0 h and 24 h data was used for the subsequent analysis.

Viable cells at original tissue (HF) dissociation, downstream target HFN cells per viable origin cell and glucose consumption per hair follicle for 5 independent cell lines were analysed in Prism.

Primary Analysis

The relationships between glucose usage per follicle, viable cell number at HF dissociation and number of downstream target HFN cells was examined by linear regression. Target HFNs were defined by number of dissociated neurosphere cells at ~DIV7 of the manufacture process, and set to zero if a HFN cell line failed any Critical Quality Attributes at the end of the manufacture process (~DIV28).

Example 3: Results

Standard Curve as Technical Validation of Assay

As a first step, the inventors validated the technical performance of the glucose colorimetric assay. Media of known concentration was serially diluted to serve as gold-standard benchmark and compared against the Abcam Glucose Assay. As shown in FIG. 1 below, the assay performed with near-perfect quantitative precision.

Glucose Usage Predicts the Portion of Target Cells Harvested Per Live Cell in Source Tissue Next, the inventors used the assay to measure glucose consumption in n=5 independent HFN cell lines.

Figure 2:
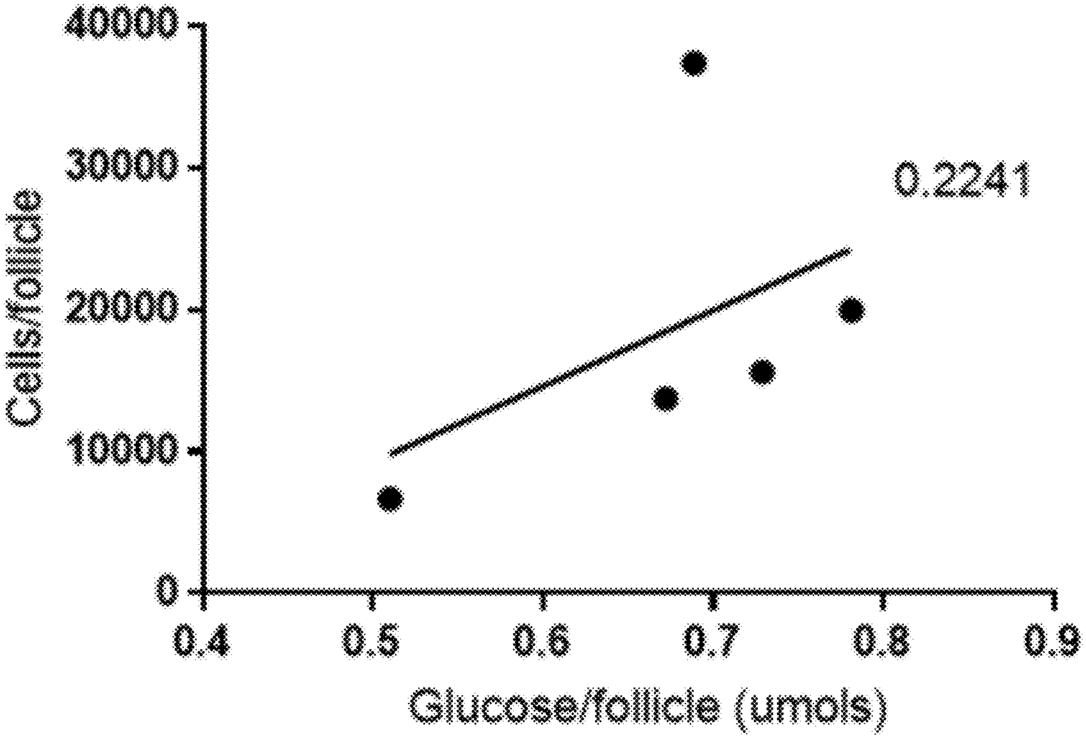
FIG. 2: Glucose consumption per follicle does not correlate with total viable cells harvested at tissue dissociation. The number of cells produced at hair follicle dissociation has little impact on the number of cells produced at tissue dissociation. The figure is a linear regression model with a goodness of fit ($R^2$) of 0.2241, with a p value of 0.4206 indicating that the variables are not significantly correlated. The figure represents the cells produced at tissue dissociation per follicle for five independent HFN cell lines.

Glucose usage per follicle during the 24 h enrichment phase of tissue processing does not significantly predict the number of cells harvested at HF dissociation (FIG. 2). In other words, the total number of non-specific cells derived from a HF after 24 h in our holding media was not related to glucose consumption during that time.

Figure 3:
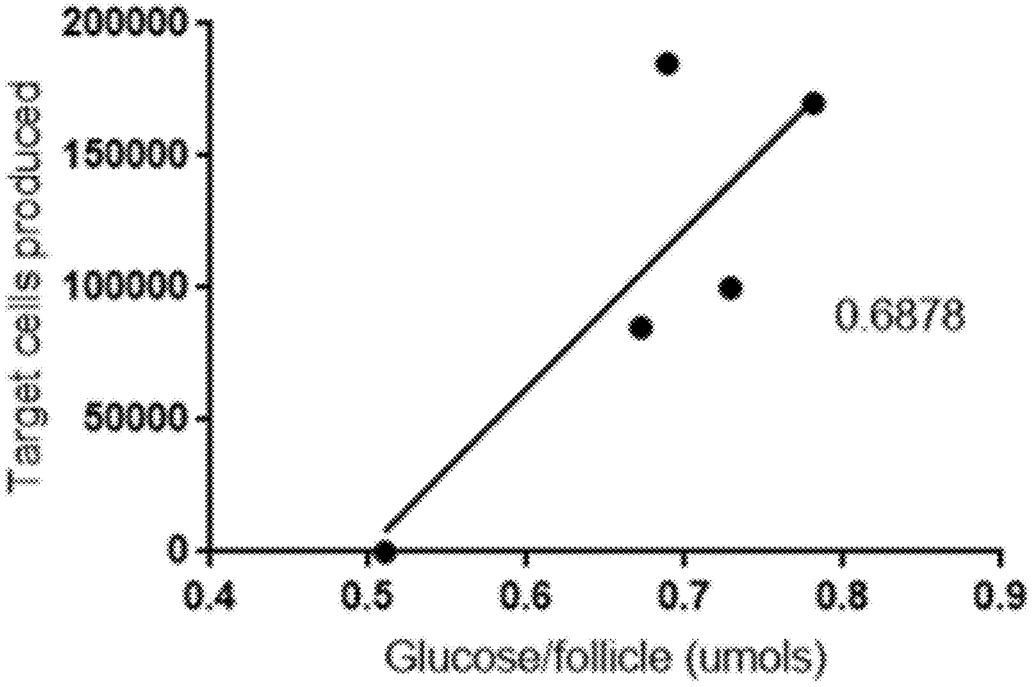
FIG. 3: Absolute number of HFN target cells produced does not strongly correlate with glucose consumption of the source hair follicle. Data represented as a linear regression model with a goodness of fit ($R^2$) of 0.6878 with a p value of 0.0825, indicating a weak positive trend that did not meet statistical significance. Based on five independent HFN cell lines.

Next, the inventors examined the relationship between 24 h HF glucose consumption and number of target HFN cells at DIV7 (post neurosphere dissociation). As shown in FIG. 3 there was a weak positive trend that did not meet statistical significance (p=0.083).

Figure 4:
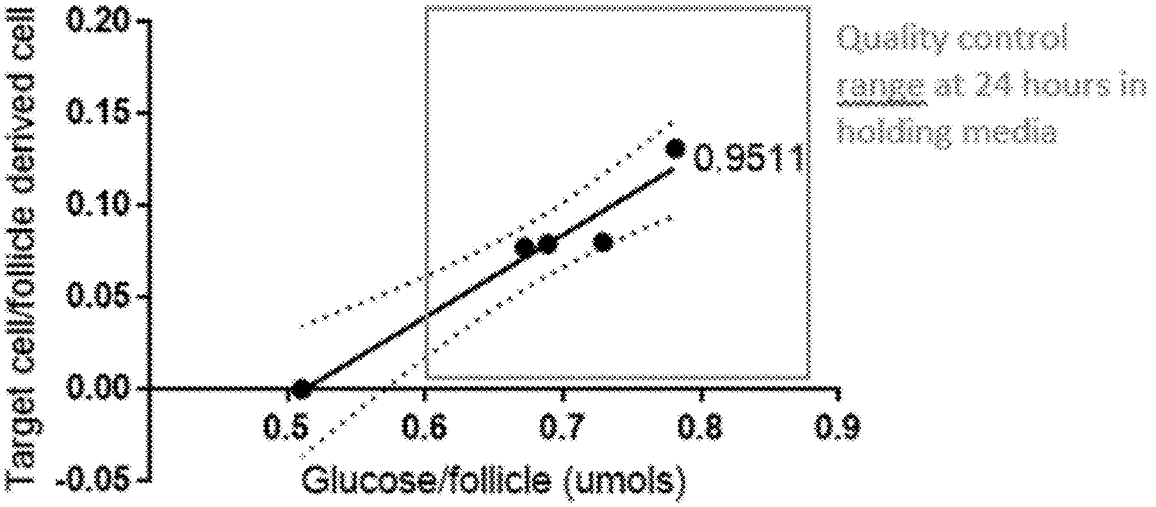
FIG. 4: Number of HFN target cells relative to cell number at hair follicle dissociation is strongly predicted by glucose consumption of source hair follicles. The number of target cells at neurosphere dissociation normalised to the number of live cells at HF dissociation correlates with the glucose consumption during the first 24 h of incubation in conditioned media. Data represented as a linear regression model with a goodness of fit ($R^2$) of 0.9511 with a p value of 0.0047 indicating that the variables are significantly correlated. Based on five independent HFN cell lines.

However, after combining both these outcome metrics (HFN target cells normalised to the number of total live cells in the original HF population), the inventors found a remarkably strong and significance predictive relationship with glucose consumption in the first 24 h (R2 0.95, p<0.005. FIG. 4). These data clearly show that a higher glucose consumption by individual HFs in the first 24 h almost perfectly predicts number of downstream HFNs relative to all viable cells in the donor source tissue.

Example 4: Discussion and Conclusions

The quality of a bioanalytical method is highly dependent on the linearity of the calibration curve. FIG. 1 shows the standard curve for the glucose assay and the R2 of 0.99 demonstrates an exceptionally precise readout. This simple assay is cheap and cost effective and this approach to producing a standard curve easily replicated for validation of the assay in new settings.

The data reported here indicate that the average in vitro glucose usage per follicle ranges from 0.51-0.78 μmols per follicle in 24 hours depending on the donor.

The lack of relationship between glucose consumption and cell number at HF dissociation shown in FIG. 2 suggests a high degree of variation in cellular composition of donor material. In other words, glucose consumption of intact follicles did not scale with total HF cell harvest, suggesting that the metabolic profile of different donor follicles is variable, as is their cellular density. The hair follicle is comprised of multiple cell types with different metabolic profiles and this is impacted to a large extent by where the follicles are within the hair cycle.

The non-significant trend relationship between follicle glucose consumption and target cell number (FIG. 3) changed to be strongly predictive when a more specific metric was used: target cells produced per follicle-derived cell (FIG. 4). This in effect adjusts the key outcome variable (number of HFNs post neurosphere dissociation) by the number and size of the source HFs. Using this metric, glucose consumption by whole HFs in the first 24 was remarkably linearly predictive.

At original HF dissociation, harvested cells are diverse in nature and number. These data indicate that a high glucose demand during the first 24 h of cell manufacture, whilst still as intact HFs, almost perfectly scales with a greater proportion of target HFN cells. These data suggest that increased HF glucose demand has an intimate relationship with target HFNs.

The number of target HFN cells produced per live HF cell is almost perfectly proportional to glucose usage during the first 24 h of source tissue treatment. The inventors therefore have identified one of the key determinants of HFN cell quality and quantity at the start of the cell manufacture process, and so is able to predict and control final therapeutic cell quality and quantity using a source tissue biomarker.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of determining suitability of a source tissue for generating hair-follicle derived neural precursors (HFNs), the method comprising:

obtaining a reference glucose consumption profile from intact human hair follicles that are capable of generating a viable HFN cell line;

obtaining a sample comprising hair follicles from the source tissue;

measuring a glucose consumption level of the hair follicles in the sample;

comparing the measured glucose consumption level of the hair follicles in the sample to the reference glucose consumption profile;

determining that:

the source tissue is suitable for generating HFNs when the measure glucose consumption level is equal to or greater than that of the reference glucose consumption profile; or (ii) the source tissue is unsuitable for generating HFNs when the measured glucose consumption level is less than the reference glucose consumption profile, optionally obtaining viable hair-follicle derived neural precursors (HFNs) therefrom.

2. The method of claim 1, wherein the sample comprising hair follicles from the source tissue comprises a sample comprising hair follicles from skin tissue.

3. The method of claim 1, wherein the sample comprising hair follicles is obtained from human scalp skin or from midline occipital scalp skin.

4. The method of claim 1, wherein the measured glucose consumption level of the hair follicles in the sample is determined from intact, whole hair follicles.

5. The method of claim 1, wherein the step of measuring the glucose consumption level of the hair follicles occurs within about 1 to about 24 hours, optionally between about 4 to 12 hours of collection of isolation or harvesting of the sample from a tissue donor.

6. The method of claim 1, wherein the step of measuring the glucose consumption level of the hair follicles in the sample occurs prior to a step of dissociation of the hair follicles in the sample from connective tissue and extracellular matrix.

7. The method of claim 1, wherein the reference glucose consumption profile is derived from one or more samples of hair follicles from which viable HFNs were successfully isolated.

8. The method of claim 1, wherein the sample comprising the hair follicles from a source tissue is contacted with a medium for supporting hair follicle cells prior to the step of determining the glucose consumption level of the hair follicles in the sample.

9. The method of claim 8, wherein the medium for supporting hair follicle cells comprises Williams' Medium E.

10. The method of claim 9, wherein the medium for supporting hair follicle cells is supplemented with one or more anti-refractory factors and/or one or more pro-growth factors.

11. The method of claim 10, wherein the medium for supporting hair follicle cells comprises insulin and/or sonic hedgehog (SHH) protein.

12. The method of claim 1, wherein the measured glucose consumption level is (i) directly calculated from measuring a rate of glycolysis by the hair follicles; or (ii) indirectly calculated from one or more surrogate markers of glucose metabolism, wherein the one or more surrogate markers of glucose metabolism is selected from: pyruvate, NADH, oxygen, lactate, and ATP.

13. The method of claim 1, wherein the measured glucose consumption level is normalised relative to a number of cells in the sample comprising hair follicles.

14. A method of determining if a sample of hair follicles comprises sufficient numbers of HFNs for isolation, the method comprising:

obtaining a sample comprising hair follicles;

measuring a glucose consumption level of the hair follicles in the sample;

comparing the measured glucose consumption level of the hair follicles in the sample to a reference glucose consumption profile from intact human hair follicles from which HFNs were successfully isolated;

determining that (i) the sample of hair follicles comprises sufficient numbers of HFNs for isolation when the measured glucose consumption level of the follicles in the sample is equal to or greater than that of the reference glucose consumption profile; or (ii) the sample of hair follicles does not comprise sufficient numbers of HFNs for isolation when the measured glucose consumption level of the follicles is less than that of the reference glucose consumption profile, optionally obtaining viable hair-follicle derived neural precursors (HFNs) therefrom.

15. An improved method of generating neuronal precursor cells from a sample of hair follicles or a sample of hair follicle cells, the method comprising:

treating a sample of hair follicles or a sample of hair follicle cells in conditions enabling a transition of hair follicle cells to a growth phase, thereby forming a sample of conditioned hair follicles or hair follicle cells;

measuring a glucose consumption level of the conditioned hair follicles or hair follicle cells;

comparing the measured glucose consumption level of the conditioned hair follicles or hair follicle cells to a reference glucose consumption profile representative of hair follicles or hair follicle cells from which viable HFNs were isolated; and treating the conditioned hair follicles or hair follicle cells in conditions enabling enrichment of cells expressing neuronal lineage biomarkers when the measured glucose consumption level of the conditioned hair follicles or hair follicle cells is equal to or greater than that of the reference glucose consumption profile, thereby generating a composition of neuronal precursor cells from a sample of hair follicles or a sample of hair follicle cells.

16. The method of claim 15, wherein the conditions enabling enrichment of cells expressing neuronal lineage biomarkers comprise contacting the conditioned hair follicles or hair follicle cells with one or more enzymes or subjecting the conditioned hair follicles or hair follicle cells to mechanical treatment to dissociate hair follicles from connective tissue and/or extracellular matrix present in the sample.

17. The method of claim 15, wherein the conditions enabling enrichment of cells containing neuronal lineage biomarkers comprise culturing the conditioned hair follicles or hair follicle cells with a culture medium and conditions for promoting formation and expansion of neurospheres.

18. The method of claim 17, wherein the culture medium and conditions for promoting formation and expansion of neurospheres comprise EGF and FGF2.

* * * * *